US006395293B2

(12) United States Patent
Polson et al.

(10) Patent No.: US 6,395,293 B2
(45) Date of Patent: *May 28, 2002

(54) BIODEGRADABLE IMPLANT PRECURSOR

(75) Inventors: Alan M. Polson; Deryl D. Swanbom; Richard L. Dunn; Charles P. Cox; Richard L. Norton; Bryan K. Lowe; Kenneth S. Peterson, all of Fort Collins, CO (US)

(73) Assignee: Atrix Laboratories, Fort Collins, CO (US)

( * ) Notice: Subject to any disclaimer, the term of this patent is extended or adjusted under 35 U.S.C. 154(b) by 0 days.

(21) Appl. No.: 09/520,735

(22) Filed: Mar. 8, 2000

Related U.S. Application Data

(63) Continuation of application No. 08/883,260, filed on Jun. 26, 1997, now Pat. No. 6,071,530, which is a continuation of application No. 08/294,754, filed on Aug. 23, 1994, now Pat. No. 5,660,849, which is a continuation of application No. 08/127,642, filed on Sep. 28, 1993, now Pat. No. 5,487,897, and a continuation-in-part of application No. 07/783,512, filed on Oct. 28, 1991, now Pat. No. 5,324,519, which is a continuation-in-part of application No. 07/384,416, filed on Jul. 24, 1989, now Pat. No. 5,077,049.

(51) Int. Cl.[7] .................................................. A61F 2/00
(52) U.S. Cl. ........................ 424/426; 424/424; 424/423; 424/422; 514/772.3; 514/785
(58) Field of Search ................................ 424/422, 423, 424/424, 425, 426

(56) References Cited

U.S. PATENT DOCUMENTS

| 2,155,658 | A | 4/1939 | Hermann, et al. |
| 3,068,188 | A | 12/1962 | Beste, et al. |
| 3,218,283 | A | 11/1965 | Miller, et al. |
| 3,219,527 | A | 11/1965 | Gurney |
| 3,328,246 | A | 6/1967 | Gottfried, et al. |
| 3,458,622 | A | 7/1969 | Hill |
| 3,463,158 | A | 8/1969 | Schmitt, et al. |

(List continued on next page.)

FOREIGN PATENT DOCUMENTS

| CA | 1261549 | 9/1989 |
| DE | 2917037 | 4/1980 |
| EP | 0140766 | 5/1985 |
| EP | 0169016 | 7/1985 |

(List continued on next page.)

OTHER PUBLICATIONS

"Encylopedia of Polymer Science and Engineering", *John Wiley & Sons, Inc., vol. 2*, 236–237, (1985).

Billmeyer, *Textbook of Polymer Science, 3rd Ed.*, 390–301.

Gilding, D.K., Biodegradable Polymers [for implant], *Biodegradable Clin. Implant Mater*, 1981, 209–232.

(List continued on next page.)

*Primary Examiner*—James M. Spear
(74) *Attorney, Agent, or Firm*—Schwegman, Lundberg, Woessner & Kluth, P.A.

(57) ABSTRACT

The invention is directed to a biodegradable implant precursor having a two-part structure made of an outer sac and a liquid content. The implant precursor is composed of a biodegradable, water-coagulable thermoplastic polymer and a water-miscible organic solvent. When administered to an implant site in an animal, the implant precursor will solidify in situ to a solid, microporous matrix by dissipation of the organic solvent to surrounding tissue fluids and coagulation of the polymer. The invention also includes methods of making the implant precursor, an apparatus for forming the precursor, and a kit containing the apparatus. Also provided are methods of using the implant precursor for treating a tissue defect in an animal, for example, for enhancing cell growth and tissue regeneration, wound and organ repair, nerve regeneration, soft and hard tissue regeneration, and the like, for delivery of biologically-active substances to tissue or organs, and other like therapies.

28 Claims, 2 Drawing Sheets

U.S. PATENT DOCUMENTS

| | | |
|---|---|---|
| 3,520,949 A | 7/1970 | Shepard, et al. ............ 260/857 |
| 3,696,811 A | 10/1972 | Chen, et al. |
| 3,755,558 A | 8/1973 | Scribner, et al. |
| 3,760,034 A | 9/1973 | Critchfield, et al. |
| 3,767,784 A | 10/1973 | Gluck ........................ 424/28 |
| 3,887,699 A | 6/1975 | Yolles |
| 3,919,773 A | 11/1975 | Freeman |
| 3,931,678 A | 1/1976 | O'Sullivan, et al. |
| 3,935,308 A | 1/1976 | Wise, et al. |
| 3,939,111 A | 2/1976 | Schollenberger, et al. |
| 3,949,073 A | 4/1976 | Daniels, et al. |
| 3,975,350 A | 8/1976 | Hudgin, et al. |
| 4,088,798 A | 5/1978 | Michaelis |
| 4,127,127 A | 11/1978 | Wong, et al. |
| 4,148,871 A | 4/1979 | Pitt, et al. |
| 4,161,948 A | 7/1979 | Bichon |
| 4,294,753 A | 10/1981 | Urist |
| 4,408,023 A | 10/1983 | Gould, et al. |
| 4,439,420 A | 3/1984 | Mattel, et al. |
| 4,443,430 A | 4/1984 | Mattel, et al. |
| 4,447,562 A | 5/1984 | Ivani |
| 4,450,150 A | 5/1984 | Sidman ...................... 424/1.1 |
| 4,451,452 A | 5/1984 | Deibig, et al. |
| 4,455,256 A | 6/1984 | Urist |
| 4,491,479 A | 1/1985 | Lauchenauer |
| 4,506,681 A * | 3/1985 | Mundell ................... 128/92 D |
| 4,526,909 A | 7/1985 | Urist, et al. |
| 4,526,938 A | 7/1985 | Churchill et al. |
| 4,563,489 A | 1/1986 | Urist |
| 4,568,536 A | 2/1986 | Kronenthal, et al. |
| 4,570,629 A | 2/1986 | Widra |
| 4,582,640 A | 4/1986 | Smestad, et al. |
| 4,595,713 A | 6/1986 | St. John |
| 4,596,574 A | 6/1986 | Urist |
| 4,614,787 A | 9/1986 | Szycher, et al. |
| 4,619,989 A | 10/1986 | Urist |
| 4,631,188 A | 12/1986 | Stoy, et al. |
| 4,650,665 A | 3/1987 | Kronenthal, et al. |
| 4,663,077 A | 5/1987 | Rei, et al. |
| 4,677,139 A | 6/1987 | Feinmann et al. |
| 4,702,917 A | 10/1987 | Schindler ................... 424/422 |
| 4,715,369 A | 12/1987 | Suzuki, et al. |
| 4,745,160 A | 5/1988 | Churchill, et al. |
| 4,761,471 A | 8/1988 | Urist |
| 4,767,627 A | 8/1988 | Caldwell, et al. |
| 4,767,861 A | 8/1988 | Boulware |
| 4,772,470 A | 9/1988 | Inoue, et al. |
| 4,774,227 A | 9/1988 | Piez, et al. |
| 4,780,320 A | 10/1988 | Baker, et al. |
| 4,789,732 A | 12/1988 | Urist |
| 4,793,336 A | 12/1988 | Wang |
| 4,795,804 A | 1/1989 | Urist |
| 4,800,219 A | 1/1989 | Murdoch, et al. |
| 4,804,691 A | 2/1989 | English, et al. ............. 523/118 |
| 4,857,456 A | 8/1989 | Urist |
| 4,857,602 A | 8/1989 | Casey, et al. |
| 4,863,472 A | 9/1989 | Tormala, et al. .............. 623/16 |
| 4,892,733 A | 1/1990 | Bichon, et al. |
| 4,894,373 A | 1/1990 | Urist |
| 4,902,296 A | 2/1990 | Bolander, et al. |
| 4,904,478 A | 2/1990 | Walsdorf, et al. |
| 4,905,680 A | 3/1990 | Tunc |
| 4,911,931 A | 3/1990 | Baylink |
| 4,912,141 A | 3/1990 | Kronman |
| 4,916,241 A | 4/1990 | Hayward, et al. |
| 4,919,939 A | 4/1990 | Baker |
| 4,920,203 A | 4/1990 | Tang, et al. |
| 4,921,697 A | 5/1990 | Peterlik, et al. |
| 4,932,973 A | 6/1990 | Gendler |
| 4,933,182 A | 6/1990 | Higashi, et al. |
| 4,938,763 A | 7/1990 | Dunn, et al. ............. 604/891.1 |
| 4,939,131 A | 7/1990 | Benedict, et al. |
| 4,942,157 A | 7/1990 | Gall, et al. |
| 4,946,870 A | 8/1990 | Partain, III, et al. |
| 4,961,707 A | 10/1990 | Magnusson, et al. |
| 4,981,696 A | 1/1991 | Loomis, et al. |
| 4,983,689 A | 1/1991 | Yu |
| 5,007,940 A | 4/1991 | Berg |
| 5,013,553 A | 5/1991 | Southard, et al. |
| 5,077,049 A | 12/1991 | Dunn, et al. ................. 424/426 |
| 5,149,052 A | 9/1992 | Stoy, et al. ................. 249/105 |
| 5,250,584 A | 10/1993 | Ikada, et al. |
| 5,278,201 A | 1/1994 | Dunn, et al. ................. 523/113 |
| 5,278,202 A | 1/1994 | Dunn, et al. ................. 523/113 |
| 5,286,763 A | 2/1994 | Gerhart, et al. |
| 5,324,519 A | 6/1994 | Dunn et al. ................. 424/426 |
| 5,324,520 A | 6/1994 | Dunn, et al. |
| 5,340,849 A | 8/1994 | Dunn, et al. |
| 5,368,859 A | 11/1994 | Dunn, et al. |
| 5,487,897 A | 1/1996 | Polson et al. ............... 424/426 |
| 5,599,552 A | 2/1997 | Dunn et al. ................. 424/423 |
| 5,660,849 A | 8/1997 | Polson et al. ............... 424/426 |
| 5,702,716 A * | 12/1997 | Dunn et al. ................. 424/422 |
| 6,071,530 A | 6/2000 | Polson et al. ............... 424/426 |

FOREIGN PATENT DOCUMENTS

| | | | |
|---|---|---|---|
| EP | 0171173 | 7/1985 | |
| EP | 0241178 | 3/1987 | |
| EP | 0244118 | 4/1987 | |
| EP | 0271831 | 6/1988 | |
| EP | 0297535 | 1/1989 | |
| EP | 0430474 | 6/1991 | ............ A61K/9/70 |
| EP | 0560014 | 1/1993 | |
| EP | 0537559 | 4/1993 | |
| EP | 0539751 | 5/1993 | ............ A61K/9/00 |
| EP | 0649662 | 8/1994 | |
| FR | 2635685 | 3/1990 | |
| GB | 2197658 | 5/1988 | |
| GB | 2223027 | 3/1990 | ............ A61L/15/00 |
| JP | 5-504941 | 7/1993 | ............ A61K/6/00 |
| JP | 6-196132 | 7/1994 | ............ H01J/65/04 |
| NZ | 226514 | 2/1990 | |
| WO | 85/00969 | 3/1985 | |
| WO | 85/02092 | 5/1985 | |
| WO | 85/03445 | 8/1985 | |
| WO | 8503445 | 8/1985 | |
| WO | 89/01006 | 2/1989 | |
| WO | 90/00067 | 1/1990 | |
| WO | 90/07308 | 7/1990 | |
| WO | 91/01126 | 2/1991 | ............ A61K/6/00 |

OTHER PUBLICATIONS

Holland, et al., *Journal of Controlled Release*, 4, 155–180, (1986).

Juni, K., et al., "Control of Release Rate of Bleomycin from Polyactic Acid Microspheres by Additives", *Chem. Pharm. Bull.* 33(4)1, 1609, (1985).

Magnusson, et al., "New Attachment Formation Following Controlled Tissue Regeneration Using Biodegradable Membranes", *J. Periodontol.* 59, 1–6, (1988).

Salonen, et al., "Migration of Epithelial Cells on Materials Used in Guided Tissue Regeneration", *J. Periodont. Res.* 25, 215–221, (1990).

* cited by examiner

BIODEGRADABLE IMPLANT PRECURSOR

CROSS-REFERENCE TO RELATED APPLICATIONS

This patent application is a continuation of U.S. patent application Ser. No. 08//883,260, filed Jun. 26, 1997 (now U.S. Pat. No. 6,071,530), which is a continuation of U.S. patent application Ser. No. 08/294,754, filed Aug. 23, 1994 (now U.S. Pat. No. 5,660,849), which is a continuation of U.S. patent application Ser. No. 08/127,642, filed Sep. 28, 1993 (now U.S. Pat. No. 5,487,897), a continuation-in-part of U.S. patent application Ser. No. 07/783,512, filed Oct. 28, 1991, which is a continuation-in-part of U.S. patent application Ser. No. 07/384,416, filed Jul. 24, 1989 (now U.S. Pat. No. 5,077,049).

BACKGROUND OF THE INVENTION

In the course of periodontal disease, infection of gingival tissue by plaque bacteria causes the ligaments attaching the gum and teeth to recede, decalcifies the bony structure holding the teeth roots to the bone, and forms periodontal pockets in the gingival tissue adjacent the teeth. Successful periodontal restoration is known to occur if periodontal ligament cells are allowed to colonize root surfaces preferentially over gingival epithelial cells, gingival fibroblasts or osteoblasts. Surgery alone, however, does not result in restoration of lost periodontium.

In an attempt to promote and achieve periodontal restoration, implant techniques have been developed. For example, microporous membranes, such as the Millipore® filter and GORE-TEX® membranes, have been developed for use in periodontal tissue regeneration. Typically, the periodontal flap is cut, and the microporous membrane is surgically inserted to cover the surface of the tooth root and to physically occlude epithelial cells from apically migrating along the root surface.

These membranes have several drawbacks. Besides providing variable results, a second surgical entry is needed to remove the membrane after tissue regeneration has been achieved because the membranes are not biodegradable. There is also a higher incidence of infection in connection with their use.

To preclude surgical removal of an implant, membranes made of bioabsorbable material, such as microfibrillar collagen, polylactic acid, and polygalactin (Vicryl®) mesh have been used. Fitting and positioning these membranes to the implant site is cumbersome and time-consuming, and the therapeutic effect of these membranes has been unpredictable. In addition, the degradation time of membranes composed of collagen has been variable, and the risk of adverse immunological reaction to this foreign protein material in the body presents a major concern.

A liquid system containing a biodegradable polymer has been developed wherein the solution is injected into an implant site, and solidifies in situ to form a biodegradable implant having a solid microporous matrix. Advantageously, the implant does not require surgical removal. However, controlled delivery and containment of a liquid system within a particular area within the implant site is difficult, and the liquid may spread to areas other than the implant site.

Therefore, there is a need for an article which will facilitate the controlled placement in an implant site of a liquid polymer solution for forming an implant. A further need is to develop a precursor to a solid implant which is neither all-liquid nor all-solid but will solidify in situ to form a solid microporous implant. There is also a need for a precursor to a solid implant that can be applied to a tissue defect in an animal and shaped or molded in situ to conform to the defect. Yet another need is to develop in vivo and ex vivo methods of making an implant precursor having such characteristics.

SUMMARY OF THE INVENTION

These and other goals are achieved by the present invention which is directed to an implant precursor for implantation in an animal, such as a human or other mammal, which will eventually harden in situ to a solid implant having a microporous matrix. The invention also provides a method of making and using the implant precursor. An apparatus is also provided for forming an implant precursor ex vivo, and a kit containing the apparatus.

The implant precursor is a two-part structure composed of an outer sac with a liquid content. The implant precursor is composed of a biocompatible, biodegradable and/or bioerodible, water-coagulable thermoplastic polymer or copolymer which is substantially insoluble in an aqueous media, and a pharmaceutically-acceptable, water-soluble organic solvent. The two-part structure of the implant precursor is formed by contacting a portion of a water-coagulable polymer solution with water or other aqueous medium, whereupon the solvent dissipates into the aqueous medium. This causes the polymer on the surface of the portion of polymer solution adjacent the aqueous medium to coagulate to form an outer sac having a firm consistency ranging from gelatinous to waxen-like, while the solution inside the sac (i.e., sac contents) remains a liquid. The sac contents of the implant precursor may range in consistency from watery to slightly viscous.

The implant precursor may-be applied to an implant site in an animal, such as a void, a defect, surgical incision, and the like, in or on a hard or soft tissue. Once placed in the implant site, the implant precursor eventually forms a solid microporous implant by the dissipation of the organic solvent into surrounding tissue fluids and the further coagulation of the polymer. Preferably, the matrix of the resulting implant has a two-layered pore structure with a highly porous inner core portion and a comparatively less porous outer surface layer or skin. Pores are formed in the solid matrix of the implant by dissipation of the solvent out of the composition into surrounding tissue fluids. Optionally, the implant precursor may include a separate pore-forming agent that is capable of generating pores within the polymer matrix of the solid implant, as for example, sucrose, sodium chloride, a cellulose-based polymer, and the like.

The resulting solid implant is biodegradable, bioabsorbable, and/or bioerodible, and will be gradually absorbed into the surrounding tissue fluids, as for example, blood serum, lymph, cerebral spinal fluid (CSF), saliva, and the like, and become disintegrated through enzymatic, chemical or cellular hydrolytic action. Generally, the implant will be absorbed over a period of up to about 2 years to about 3 years, preferably within about 1–9 months, preferably within about 60–180 days. The implant may be used, for example, for selective enhancement of cell growth and tissue regeneration, delivery of biologically-active substances to the animal, and the like.

The implant precursor may also include a biologically-active agent, or bioactive agent, as for example, an anti-inflammatory agent, an antiviral agent, an antibacterial or antifungal agent useful for treating and preventing infections in the implant site, a growth factor, a hormone, and the like. The implant resulting from the in situ coagulation of the implant precursor, may then serve as a system for delivering the biologically-active agent to the animal.

A release rate modification agent may also be included in the implant precursor for controlling the rate of breakdown of the implant matrix and/or the rate of release of a bioactive agent in vivo from the implant matrix. Examples of suitable substances for inclusion as a release rate modification agent include dimethyl citrate, triethyl citrate, ethyl-heptanoate, glycerin, hexanediol, and the like.

The invention also includes a method of making the implant precursor. The implant precursor may be formed in vivo or ex vivo by (a) coating the surface of a suitable support substrate with an effective amount of an aqueous medium to form a layer; (b) dispensing onto the aqueous layer, an effective amount of a liquid polymer solution made of a water-coagulable, biodegradable thermoplastic polymer such as polylactide, polycaprolactone, polyglycolide, or copolymer thereof, and a water-soluble, pharmaceutically-acceptable organic solvent such as N-methyl-2-pyrrolidone; (c) applying an effective amount of an aqueous medium onto the surface of the polymer solution; and (d) allowing the polymer adjacent the aqueous medium to coagulate to form the implant precursor having an outer sac with a liquid content. Preferably, the thickness of the implant precursor is controlled, for example, by compressing the coagulating polymer mass between two solid flat surfaces such as a glass plate, porous plastic, and the like. The aqueous medium is applied onto the surface of the support substrate and the surface of the polymer solution in a minor but effective amount to initiate coagulation of the polymer to form the outer sac of the implant precursor.

The implant precursor may be formed in vivo by dispensing the polymer solution onto a soft or hard tissue or other support substrate in the body of an animal. The precursor may also be formed ex vivo by dispensing the polymer solution onto a support substrate made, for example, from glass, a porous plastic, sintered stainless steel, porcelain, bone material, and other like materials.

In a variation of forming an implant precursor, an amount of the foregoing liquid polymer solution is applied to the surface of the support substrate to form a line which delineates a boundary around a defined area. The implant precursor may then be formed within the confines of the boundary line area. When the foregoing boundary line is formed on a tissue defect in vivo, an implant precursor may be prepared outside the body and applied to the defect within the confines of the boundary line.

Optionally, a support layer may be applied to the tissue surface to provide an adhesive substrate for securing the implant precursor onto the surface of the tissue defect. Useful substances for forming an adhesive support layer include, for example, the foregoing liquid polymer solution, a water-soluble substance such as gelatin, and the like. The support layer may be in the form of a bead, a film or coating, and the like, having a thickness as desired.

The invention also includes an apparatus for forming an implant precursor ex vivo. The apparatus is preferably a two-part assembly comprising support means for maintaining the polymer solution on a surface during formation of an implant precursor such as a porous plate or block, and means for compressing the polymer solution during formation of the implant precursor. Preferably, the support means and compressing means are connected together by hinging means positioned along one edge of the support means and the compressing means, such that the compressing means may be pivoted and placed onto the polymer solution on the support means. The support means and/or compressing means are preferably made of a porous material, as for example, a porous plastic, sintered stainless steel, porcelain, and other like materials which are absorptive to water. An aqueous medium is applied as a layer over the surface of the support means, the polymer solution applied over the aqueous layer, and a second aqueous layer is applied over the polymer solution. Preferably, two or more spacers such as a washer, are arranged on the surface of the support means to form a defined area thereinbetween, and the implant precursor is formed on the area between the spacers. The compressing means is then positioned over the support means with the spacers and coagulating polymer solution sandwiched thereinbetween, preferably compressing the coagulating polymer mass. The support means and compressing means of the apparatus are maintained in a sandwich arrangement until the outer sac of the implant precursor is formed. The support means and compressing means are then separated and the resulting implant precursor is removed from the apparatus, trimmed as desired, and placed into the implant site.

Also provided is a kit containing, in combination, the precursor-forming apparatus, one or more barrier means, an amount of the aforedescribed polymer solution in one or more vials or other containers, and an amount of an aqueous medium preferably a phosphate buffered saline in one or more vials or other like container. The kit may also include a tweezers or other like means for picking up the formed implant precursor; a calibrated tweezers or other like means for measuring the dimensions of the tissue defect and/or the implant precursor; a gridded template or other like means for measuring the dimensions of the implant precursor; a scalpel, razor or other like means for trimming the implant precursor to a desired size; and/or a cotton pad or other like means for blotting the aqueous medium from the surface of the implant precursor.

The invention also includes a method for treating a tissue defect in an animal. The implant precursor may be used, for example, for enhancing cell growth and tissue regeneration, wound and organ repair, nerve regeneration, soft and hard tissue regeneration, and the like. According to the invention, the foregoing implant precursor is applied to the tissue defect and allowed to coagulate to an implant having a solid microporous matrix.

As used herein, the term "implant site" is meant to include a site, in or on which the implant precursor is formed or applied, as for example, a soft tissue such as muscle or fat, or a hard tissue such as bone. Examples of implant sites include a tissue defect such as a tissue regeneration site; a void space such as a periodontal pocket, surgical incision or other formed pocket or cavity; a natural cavity such as the oral, vaginal, rectal or nasal cavities, the cul-de-sac of the eye, and the like; and other sites into which the implant precursor may be placed and formed into a solid implant. The term "biodegradable" means that the polymer and/or polymer matrix of the implant will degrade over time by the action of enzymes, by hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the polymer matrix will be broken down and absorbed within the human body, for example, by a cell, a tissue, and the like Since the implant precursor does not flow like a liquid, it provides easy manipulation and placement of a liquid polymer system for forming an implant on a select area of a tissue defect without the uncontrolled flow of the polymer solution outside the area of the implant site. The present implant precursor provides a system for forming an implant with a desired thickness, size, and shape. Unlike a solid implant, the implant precursor is easy to manipulate and may be shaped and molded within the defect site as it solidifies. Advantageously, the moldability of the implant precursor allows it to conform to irregularities, crevices, cracks, holes, and the like, in the tissue defect site. In addition, the surface of the implant precursor is tacky to the touch and tends to remain in place where it is applied to a tissue defect.

DETAILED DESCRIPTION OF THE INVENTION

Figure 1:
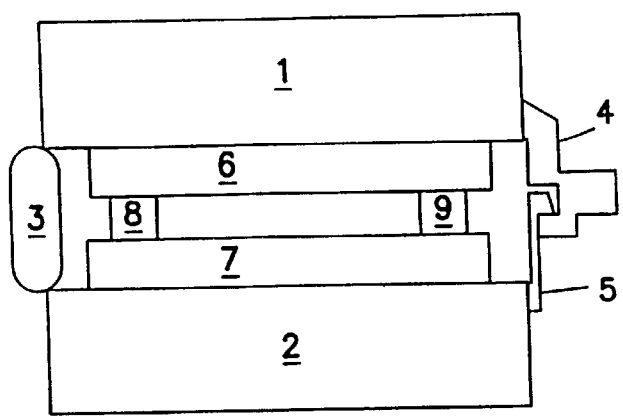
FIG. 1 is a perspective view of an embodiment of a precursor-forming apparatus of the invention.

The present invention provides an implant precursor in the form of an outer sac with a liquid content for implantation in an animal. The outer sac of the implant precursor has a firm consistency ranging from gelatinous to moldable and waxen-like. The implant precursor is composed of a biodegradable, water-coagulable, thermoplastic polymer in combination with a water-soluble, non-toxic organic solvent.

Upon implantation in the body of an animal, the organic solvent of the precursor implant dissipates into surrounding tissue fluids and the polymer coagulates to form a solid, microporous implant. The resulting solid implant has a variety of uses, as for example, a barrier system for enhancing cell growth and tissue regeneration, delivery of biologically-active agents such as drugs and medicaments, and the like.

Polymer Solution

To prepare the implant precursor, a liquid polymer solution is formulated which comprises a biodegradable, water-coagulable, thermoplastic polymer, such as a polylactide, polycaprolactone, polyglycolide, or copolymer thereof, in combination with a water-soluble, non-toxic, organic solvent, such as N-methylpyrrolidone, as disclosed in U.S. Pat. No. 4,938,763 to Dunn et al. (issued Jul. 3, 1990), the disclosure of which is incorporated by reference herein. The polymer solution may optionally include a pore-forming agent.

The polymers or copolymers are substantially insoluble in water and body fluids, and biodegradable and/or bioerodible within the body of an animal. The implant precursor and resulting solid implant are biocompatible in that neither the polymer, the solvent nor the polymer matrix cause substantial tissue irritation or necrosis at the implant site.

Thermoplastic Polymers

Thermoplastic polymers useful in the liquid polymer solution for forming the implant precursor include pharmaceutically-compatible polymers that are biodegradable, bioabsorbable, and soften when exposed to heat but return to the original state when cooled. The thermoplastic polymers are capable of substantially dissolving in a water-soluble carrier, or solvent, to form a solution. The thermoplastic polymers are also capable of coagulating, or solidifying, to form an outer sac having a firm consistency ranging from gelatinous to waxen-like, and of eventually coagulating to a solid microporous matrix upon the dissipation of the solvent component from the polymer solution, and the contact of the polymer with an aqueous medium.

Thermoplastic polymers that are suitable for use in the polymer solution generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(malic acid), poly(amino acids), poly (methyl vinyl ether), poly(maleic anhydride), chitin, chitosan, and copolymers, terpolymers, or combinations or mixtures therein. Polylactides, polycaprolactones, polyglycolides and copolymers thereof are highly preferred thermoplastic polymers.

The thermoplastic polymer is combined with a suitable organic solvent to form a solution. The solubility or miscibility of a polymer in a particular solvent will vary according to factors such as crystallinity, hydrophilicity, capacity for hydrogen-bonding, and molecular weight of the polymer. Consequently, the molecular weight and the concentration of the polymer in the solvent are adjusted to achieve desired solubility. Highly preferred thermoplastic polymers are those that have a low degree of crystallization, a low degree of hydrogen-bonding, low solubility in water, and high solubility in organic solvents.

Solvents

Suitable solvents for use in the thermoplastic polymer solution are those which are biocompatible, pharmaceutically-acceptable, miscible with the polymer ingredient and water, and capable of diffusing into an aqueous medium, as for example, tissue fluids surrounding the implant site, such as blood serum, lymph, cerebral spinal fluid (CSF), saliva, and the like. Preferably, the solvent has a Hildebrand (HLB) solubility ratio of from about 9–13(cal/cm$^3$)$^{1/2}$. The degree of polarity of the solvent should be effective to provide at least about 10% solubility in water, and to dissolve the polymer component.

Solvents that are useful in the liquid polymer solution include, for example, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, 1-dodecylazacycloheptan-2-one, and the like. Preferred solvents according to the invention include N-methyl-2-pyrrolidone, 2-pyrrolidone, dimethyl sulfoxide, ethyllactate, and propylene carbonate.

A mixture of solvents providing varying degrees of solubility for the polymer components may be used to increase the coagulation rate of polymers that exhibit a slow coagulation or setting rate. For example, the polymer may be combined with a coagulant-promoting solvent system composed of a mixture of a good solvent (i.e., solvent providing a high degree of solubility) and a poorer solvent (i.e., solvent providing a low degree of solubility) or a non-solvent (i.e., one in which the polymer is insolvent) relative to the polymer component. It is preferred that the solvent mixture contain an effective amount of a good solvent and a poorer or non-solvent, in admixture such that the polymer will remain soluble while in solution but coagulate upon dissipation or diffusion of the solvents into surrounding tissue fluids at the implant site.

The concentration of polymer in the liquid polymer composition will generally accomplish rapid and effective dissipation of the solvent and coagulation of the polymer. This concentration may range from about 0.01 gram of polymer per ml of solvent to an about saturated concentration, preferably from about 0.1 gram per ml to an about saturated concentration.

Upon contact with an aqueous medium such as water, a body fluid such as blood serum, lymph, and the like, the solvent diffuses from the polymer solution into the aqueous medium. This causes the polymer at the surface of the polymer solution and adjacent the aqueous medium to coagulate to form a two-part structure comprising-an outer sac with a liquid content. The liquid content of the implant precursor may range in consistency from watery to viscous. The outer sac may range in consistency from gelatinous to an impressionable, moldable and waxen-like. The resulting device, or implant precursor, may then be applied to an implant site. Upon implantation, the solvent from the implant precursor diffuses into the surrounding tissue fluids to form an implant having a solid polymer matrix. Preferably, the implant precursor solidifies in situ to a solid matrix within about 0.5–4 hours after implantation, preferably within about 1–3 hours, preferably within about 2 hours.

Pore-formation and Pore Forming Agents

When placed into an implant site in an animal, the implant precursor eventually coagulates to a solid, microporous matrix structure. Preferably, the matrix is composed of a microporous inner core portion and an outer microporous skin. The pores of the inner core portion are preferably substantially uniform and the skin of the solid implant is essentially non-porous compared to the porous nature of the core. Preferably, the outer skin portion of the implant has pores with diameters significantly smaller in size than these pores in the inner core portion.

Pores may be formed within the matrix of the implant by several means. The dissipation, dispersement or diffusion of the solvent out of the solidifying polymer matrix into the adjacent tissue fluids may generate pores, including pore channels, in the polymer matrix. The dissipation of the solvent from the coagulating mass creates pores within the solid implant. The size of the pores of the solid implant are in the range of about 1–1000 microns, preferably the size of pores of the skin layer are about 3–500 microns. The solid microporous implant has a porosity in the range of about 5–95%.

Optionally, a pore-forming agent may be included in the polymer solution to generate additional pores in the polymer matrix. The pore-forming agent may be any pharmaceutically-acceptable, organic or inorganic, water-soluble substance that is substantially soluble in water and body fluids, and will dissipate from the coagulating polymer matrix and/or the solid matrix of the implant into surrounding body fluids at the implant site. The porous matrices formed through the inclusion of a pore-forming agent have a pore structure in which the pores are substantially similar in size.

It is preferred that the pore-forming agent is soluble or dispersible in the organic solvent to form a uniform mixture with the polymer, either as a dispersion or suspension, or as a solution. The pore-forming agent may also be a water-immiscible substance that rapidly degrades to a water-soluble substance. Preferably, the pore-forming agent is combined with the thermoplastic polymer and solvent in admixture, before the matrix is formed. Suitable pore-forming agents that may be used in the polymer composition include, for example, sugars such as sucrose and dextrose, salts such as sodium chloride and sodium carbonate, polymers such as hydroxylpropylcellulose, carboxymethylcellulose, polyethylene glycol, and polyvinylpyrrolidone, and the like. Solid crystals that will provide a defined pore size, such as salt or sugar, are preferred.

When the implant precursor is applied to an implant site, the solvent and/or pore-forming agent dissipates into surrounding tissue fluids. This causes the formation of microporous channels within the coagulating polymer matrix. Optionally, the pore-forming agent may dissipate from the matrix into the surrounding tissue fluids at a rate slower than that of the solvent, or be released from the matrix over time by biodegradation or bioerosion of the matrix. Preferably, the pore-forming agent dissipates from the coagulating implant matrix within a short time following implantation such that a matrix is formed with a porosity and pore structure effective to perform the particular purpose of the implant, as for example, a barrier system for a tissue regeneration site, a matrix for timed-release of a drug or medicament, and the like.

Porosity of the solid implant matrix may be varied by the concentration of water-soluble or water-miscible ingredients, such as the solvent and/or pore-forming agent, in the polymer composition. For example, a high concentration of water-soluble substances in the thermoplastic composition may produce a polymer matrix having a high degree of porosity. The concentration of the pore-forming agent relative to polymer in the composition may be varied to achieve different degrees of pore-formation, or porosity, in the matrix. Generally, the polymer composition will include about 0.01–1 gram of pore-forming agent per gram polymer.

The size or diameter of the pores formed in the matrix of the solid implant may be modified according to the size and/or distribution of the pore-forming agent within the polymer matrix. For example, pore-forming agents that are relatively insoluble in the polymer mixture may be selectively included in the polymer composition according to particle size in order to generate pores having a diameter that corresponds to the size of the pore-forming agent. Pore-forming agents that are soluble in the polymer mixture may be used to vary the pore size and porosity of the implant matrix by the pattern of distribution and/or aggregation of the pore-forming agent within the polymer mixture and coagulating and solid polymer matrix.

Where the implant is used to promote guided tissue regeneration, it is preferred that the diameter of the pores in the matrix are effective to deter growth of epithelial cells and enhance growth of connective tissue cells into the polymer matrix of the implant. It is further preferred that the size of the pores and porosity of the matrix of the implant facilitate diffusion of nutrients and other growth-promoting substances such as growth factors, to cells which have grown into the matrix. Preferably, the degree of porosity of the matrix provides an implant that is capable of substantially maintaining structural integrity for the desired period of time without breakage or fracturing during use.

To provide an effective implant for bone cell regrowth and tissue regeneration, it is preferred that the diameter of the pores of the implant is about 3–500 microns, more preferably about 3–200 microns, more preferably about 75–150 microns. It is further preferred that the matrix has a porosity of about 5–95%, preferably about 25–85%, in order to provide optimum cell and tissue ingrowth into the matrix and optimum structural integrity.

Pore diameter and distribution within the polymer matrix of the solid implant may be measured, as for example, according to scanning electron microscopy methods by examination of cross-sections of the polymer matrix. Porosity of the polymer matrix may be measured according to suitable methods known in the art, as for example, mercury intrusion porosimetry, specific gravity or density comparisons, calculation from scanning electronic microscopy photographs, and the like. Additionally, porosity may be calculated according to the proportion or percent of water-soluble material included in the polymer composition. For example, a polymer composition which contains about 30% polymer and about 70% solvent and/or other water-soluble components will generate an implant having a polymer matrix of about 70% porosity.

Biologically-active Agent

Optionally, the polymer solution may include a biologically-active agent, either singly or in combination, such that the implant precursor and implant will provide a delivery system for the agent to adjacent or distant tissues and organs in the animal. Biologically-active agents which may be used alone or in combination in the implant precursor and implant include, for example, a medicament, drug, or other suitable biologically-, physiologically-, or pharmaceutically-active substance which is capable of providing local or systemic biological, physiological or therapeutic effect in the body of an animal including a mammal, and of being released from the solid implant matrix into adjacent or surrounding tissue fluids.

The biologically-active agent may be soluble in the polymer solution to form a homogeneous mixture, or insoluble in the polymer solution to form a suspension or dispersion. Upon implantation, the biologically-active agent preferably becomes incorporated into the implant matrix. As the matrix degrades over time, the biologically-active agent is released from the matrix into the adjacent tissue fluids, preferably at a controlled rate. The release of the biologically-active agent from the matrix may be varied, for example, by the solubility of the biologically-active agent in an aqueous medium, the distribution of the agent within the matrix, the size, shape, porosity, solubility and biodegradability of the implant matrix, and the like.

The polymer solution, implant precursor and implant include the biologically-active agent in an amount effective to provide the desired level of biological, physiological, pharmacological and/or therapeutic effect in the animal. There is generally no critical upper limit on the amount of the bioactive agent included in the polymer solution. The only limitation is a physical limitation for advantageous application, i.e., the bioactive agent should not be present in such a high concentration that the solution or dispersion viscosity is too high for injection. The lower limit of the amount of bioactive agent incorporated into the polymer solution will depend on the activity of the bioactive material and the period of time desired for treatment.

The biologically-active agent may stimulate a biological or physiological activity with the animal. For example, the agent may act to enhance cell growth and tissue regeneration, function in birth control, cause nerve stimulation or bone growth, and the like. Examples of useful biologically-active agents include a substance, or metabolic precursor thereof, which is capable of promoting growth and survival of cells and tissues, or augmenting the functioning of cells, as for example, a nerve growth promoting substance such as a ganglioside, a nerve growth factor, and the like; a hard or soft tissue growth promoting agent such as fibronectin (FN), human growth hormone (HGH), protein growth factor interleukin-1 (IL-1), and the like; a bone growth promoting substance such as hydroxyapatite, tricalcium phosphate, and the like; and a substance useful in preventing infection at the implant site, as for example, an antiviral agent such as vidarabine or acyclovir, an antibacterial agent such as a penicillin or tetracycline, an antiparasitic agent such as quinacrine or chloroquine.

Suitable biologically-active agents for use in the invention also include anti-inflammatory agents such as hydrocortisone, prednisone and the like; anti-bacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribarivin, interferons and the like; antineoplastic agents such as methotrexate, 5-fluorouracil, adriamycin, tumor-specific antibodies conjugated to toxins, tumor necrosis factor, and the like; analgesic agents such as salicylic acid, acetaminophen, ibuprofen, flurbiprofen, morphine and the like; local anaesthetics such as lidocaine, bupivacaine, benzocaine and the like; vaccines such as hepatitis, influenza, measles, rubella, tetanus, polio, rabies and the like; central nervous system agents such as a tranquilizer, B-adrenergic blocking agent, dopamine and the like; growth factors such as colony stimulating factor, platelet-derived growth factor, fibroblast growth factor, transforming growth factor B, human growth hormone, bone morphogenetic protein, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; anti-ulcer agents such as cimetidine hydrochloride, isopropamide iodide, and the like; bronchodilators such as metaproternal sulfate, aminophylline and the like; vasodilators such as theophylline, niacin, minoxidil, and the like; and other like substances. For other examples of biologically-active agents that may be used in the present invention, see Applicants' corresponding U.S. patent application Ser. No. 07/783,512, filed Oct. 28, 1991 U.S. Pat. No. 5,324,519, the disclosure of which is incorporated by reference herein.

Accordingly, the formed implant may function as a delivery system of drugs, medicaments and other biologically-active agents to tissues adjacent to or distant from the implant site. The biologically-active agent is preferably incorporated into the polymer matrix, and subsequently released into surrounding tissue fluids and to the pertinent body tissue or organ.

Control of Release of the Bioactive Agent

The rate of breakdown of the implant and/or release of a bioactive agent in vivo may be controlled by varying the type and molecular weight of the polymer(s), by including a release rate modification agent, and/or varying the combination and concentrations of ingredients that comprise the polymer solution.

The rate of release of a bioactive agent from the implant matrix may be modified by varying the molecular weight of the polymer included in the polymer solution. It has been found that for implant matrices formed through intermediacy of the foregoing liquid polymer solution, the release rate of a bioactive agent follows a "U" shaped curve as the molecular weight of the polymer increases. That is, the rate of release of the bioactive agent will decrease, pass through a minimum, and then again increase as the molecular weight of a polymer is increased. As a result, a polymer solution can be formulated with an optimum polymer molecular weight range for the release of a bioactive substance over a selected length of time. For example, to achieve a relatively quick release of a bioactive agent from the implant matrix, a polymer molecular weight on either side of the minimum for that particular polymer would be used in the polymer solution. For release of a bioactive agent over a relatively long period of time, a polymer molecular weight at or about the minimum for the particular polymer would be preferred.

With the present polymer system, the typical minimum rate of release of a bioactive agent from the solid implant matrix occurs at an inherent viscosity (I.V. in deciliters/gm) of about 0.2 but can vary depending on the ingredients of the polymer solution. To achieve a sustained release of the bioactive agent from the implant matrix, it is preferred to adjust the molecular weight of the polymer to at least about 0.1 inherent viscosity (I.V.) or about 2,000 molecular weight as determined by gel permeation chromatography (comparison to polystyrene). Typically, acceptable sustained release rates are obtained if the molecular weight of the polymer is below about 0.8 I.V., or a molecular weight of about 100,000. More preferably, the molecular weight is adjusted to be within a range of about 0.1–0.5 I.V., for effective sustained release. For a poly(DL-lactide) or a lactide-co-glycolide system, the desired molecular weight range is about 0.1–0.5 I.V. If a molecular weight of a specific polymer is chosen from these parameters and the release of the bioactive substance is too slow or too fast, the rate can be varied simply by determining a few experimental points along the U curve for that polymer and adjusting the molecular weight accordingly.

The molecular weight of a polymer can be varied by any of a variety of methods known in the art. The choice of method is typically determined by the type of polymer solution being formulated. For example, if a thermoplastic polymer is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

For other examples and further discussion of controlling the rate of release of a bioactive agent from the implant matrix by varying the polymer composition of the polymer solution, see Applicants' corresponding U.S. patent application Ser. No. 07/776,816, filed Oct. 15, 1991, the disclosure of which is incorporated by reference herein.

Release Rate Modification Agents

The polymer solution may include a release rate modification agent to provide controlled, sustained release of a bioactive agent from the solid implant matrix. Although not intended to be a limitation to the present disclosure, it is believed the release rate modification agent alters the release rate of a bioactive agent from the implant matrix by changing the hydrophobicity of the polymer implant.

The use of a release rate modification agent may either decrease or increase the release of the bioactive agent in the range of multiple orders of magnitude (e.g., 1 to 10 to 100), preferably up to a ten-fold change, as compared to the release of a bioactive agent from a solid matrix without the release rate modification agent. For example, naltrexone and doxycycline are substantially completely released from a polymer matrix comprised of poly(DL-lactide) within about 2–3 days ex vivo. With the addition of a release rate modification agent such as ethyl heptanoate which is hydrophobic to the polymer solution, and formation of the implant matrix through interaction of the polymer solution and an aqueous medium, the release rate of naltrexone or doxycycline can be slowed to produce substantially complete release of the drug within about seven days. With the inclusion of a greater amount of a release rate modification agent into the polymer solution, the time period of the release can be increased to about fourteen days. Other release rate modification agents which are hydrophilic such as polyethylene glycol may increase the release of the bioactive agent. By an appropriate choice of the polymer molecular weight in combination with an effective amount of the release rate modification agent, the release rate and extent of release of a bioactive agent from the implant matrix may be varied, for example, from relatively fast to relatively slow.

Useful release rate modification agents include, for example, organic substances which are water-soluble, water-miscible, or water insoluble (i.e., water immiscible), with water-insoluble substances preferred.

The release rate modification agent is preferably an organic compound which will substitute as the complementary molecule for secondary valence bonding between polymer molecules, and increases the flexibility and ability of the polymer molecules to slide past each other. Such an organic compound preferably includes a hydrophobic and a hydrophilic region so as to effect secondary valence bonding. It is preferred that a release rate modification agent is compatible with the combination of polymers and solvent used to formulate polymer solution. It is further preferred that the release rate modification agent is a pharmaceutically-acceptable substance.

Useful release rate modification agents include, for example, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$–$C_{12}$ alkanols, 2-ethoxyethanol, and the like. The release rate modification agent may be used singly or in combination with other such agents. Suitable combinations of release rate modification agents include, for example, glycerin/propylene glycol, sorbitol/glycerine, ethylene oxide/propylene oxide, butylene glycol/adipic acid, and the like. Preferred release rate modification agents include dimethyl citrate, triethyl citrate, ethyl heptanoate, glycerin, and hexanediol.

The amount of the release rate modification agent included in the polymer solution will vary according to the desired rate of release of the bioactive agent from the implant matrix. Preferably, the polymer solution contains about 0.5–15%, preferably about 5–10%, of a release rate modification agent.

For other examples and further discussion of release rate modification agents, or rate modifying agents, for use in the present invention, see Applicants' corresponding U.S. patent application Ser. No. 08/070,498 U.S. Pat. No. 5,702,716 filed Jun. 2, 1993 which is a continuation of Ser. No. 07/776,816, filed Oct. 15, 1991, now abandoned. The disclosure of which is incorporated by reference herein.

Other Factors for Release Rate Modification

The release rate of the bioactive agent from the implant matrix may also be adjusted by varying the concentration of the polymer in the polymer solution. For example, the more dilute the polymer concentration, the more readily the bioactive agent will be released from the implant matrix. For example, in a system containing about 5% flurbiprofen and a polymer concentration of about 55% poly(DL-lactide), a cumulative release of about 11.4% at day 1 and about 23% at day 7 may be provided. With a polymer concentration of about 45%, the cumulative percent release is about 23% at day 1 and about 40% at day 7.

This effect can be used in combination with other means to more effectively control the release of the bioactive agent from the implant matrix as desired. For example, by adjusting the concentration of the polymer and/or the bioactive agent, together with control of the molecular weight and the amount of the release rate modification agent, a wide range of release rates can be achieved.

The release rate of a bioactive agent from the implant matrix may also be varied by the addition of additives such as a pore forming agent, as discussed herein.

Formation of the Implant Precursor

A number of methods may be used to form the implant precursor. In general, the implant precursor is formed by dispensing a portion of the liquid polymer solution onto the surface of a support substrate. An aqueous medium is then placed in contact with the polymer solution. Solvent then diffuses out of the polymer solution and the aqueous medium diffuses into the solution. This causes coagulation of the polymer adjacent to the aqueous medium to form the outer sac of the implant precursor.

Suitable support substrates include, for example, hard or soft tissue of the animal or an ex vivo material, as for example, glass, stainless steel, porcelain, solid plastic or porous plastic. These ex vivo materials may optionally have either an attached layer of a different material, such as a nylon filter, or a coating or a surface treatment or an additive that allows the support to absorb or wick an aqueous medium. Aqueous media can be blood, saliva or other body fluids when the substrate is in the animal. Aqueous media which can be used either in vivo or ex vivo included water and saline solutions. Other aqueous media can be used if they cause coagulation of the polymer solution and are clinically acceptable.

The aqueous medium can be present at the surface of the support substrate or inside the support substrate prior to the dispensing of the polymer solution or the aqueous medium can be applied on top and around the polymer solution after it is in place. In this last case coagulation of the bottom surface of the polymer solution requires the aqueous medium to travel underneath the polymer solution.

The amount of aqueous medium used and the time that the polymer solution and aqueous medium are held in contact depends on the composition of the polymer solution and the aqueous medium, the nature of the support substrate, the geometry of the apparatus, the amount and dimensions of the polymer solution and the consistency desired for the implant precursor. For a given procedure and set of materials the consistency of the implant precursor can be varied from gelatinous to formable and impression-retaining to fairly rigid by increasing the time the polymer solution and aqueous medium are in contact.

After the implant precursor has been formed, the aqueous medium may be removed by tipping the support and/or the implant precursor to allow the aqueous layer to run off or by blotting the aqueous layer with an absorbent material such as a cotton swab, gauze pad or a sponge. The implant precursor may optionally then be trimmed to the desired size and shape and then placed in the implant site. It is trimmed and implanted into the animal within about 1 to 60 minutes, preferably 1 to 10 minutes, of the conclusion of the coagulation process. If not implanted or placed back into contact with an aqueous medium, the implant precursor will soften and eventually revert to an all liquid phase. This process is caused by an interaction between the outer sac layer and the liquid contents. The solvent and aqueous medium redistribute in the implant precursor which destroys the sac formed in the coagulation process and results in one continuous liquid phase.

The dimensions of the implant precursor can be controlled by a number of methods. It is preferred that the thickness of the implant precursor is about 300–1500 $\mu$m, preferably about 600–1200 $\mu$m. The length and width desired depend on the dimensions of the implant site in the animal. In the preferred methods the thickness is controlled during the coagulation process and the length and width are controlled in a subsequent trimming step. The polymer solution is dispensed onto a flat support substrate and a second flat piece of support substrate is placed on top of the polymer solution and forced down causing the polymer solution to thin out and spread until the desired gap between the support substrates is obtained. This gap may be defined by spacers which hold the support substrate pieces apart or other means. The aqueous medium may be present during this process or applied after this process. The coagulation of the polymer solution in this defined space results in a sheet of implant precursor material with a center section of substantially uniform thickness with thinner portions at the edges. The implant precursor is then cut out of the center section of the sheet using a razor blade, surgical prep blade, scalpel or other means. This trimming step allows control of the implant precursor length, width and shape.

Alternate methods of controlling the dimensions of the implant precursor include dispensing the polymer solution onto a support substrate on which the desired area (i.e., width, length) have been defined by some type of barrier. They can be then controlled as previously described or by drawing a flat article such as a spatula across the surface of the coagulating polymer mass or like means. The polymer solution may also be dispensed into a recessed area or void as, for example, in a pre-cast die or mold or template, or other like device, which has the dimensions (i.e., width, length, depth or thickness) of the implant precursor. Additional amounts of the polymer solution may be applied to the surface(s) or edges of the coagulating polymer mass to adjust the dimensions.

Various devices may be used to form the implant precursor. One such device, which may be used ex vivo or in vivo, is a "tweezer wiper". A "tweezer wiper" is constructed by attaching a plate with a hole or a wire loop to one blade of the tweezer at a right angle to the tweezer blades such that the second blade sweeps across the surface of the plate or wire loop when the tweezer blades are spread apart. The plate or wire loop is placed on the tissue or ex vivo support substrate os that the hole in the pate or the inside of the wire loQp defines the area for the implant precursor. The polymer solution is then dispensed into this area and leveled off to control the thickness by passing the second blade of the tweezer over the polymer solution. An aqueous medium is then applied to cause coagulation. Alternatively, the aqueous medium is applied prior to the leveling procedure. Once the implant precursor is sufficiently coagulated the "tweezer wiper" is separated from the substrate. The resulting implant precursor can then be left in place in the in vivo case or otherwise used according to the method of the invention.

In another embodiment of the invention, an implant precursor may be formed in vivo or ex vivo by forming a boundary line on the surface of the support substrate to contain the polymer solution within a confined area. To form the boundary line on a substrate, an amount of water or other aqueous medium is applied as a coating on the surface of the support substrate, the polymer solution is dispensed as a line over the water layer to define a confined area, and an amount of water is then applied to the surface of the polymer solution resulting in surface coagulation of the polymer solution. The resulting boundary line is a two-part, tube-like structure made of an outer sac with a liquid center. An implant precursor may then be formed within the confines of the boundary line by dispensing an amount of the polymer solution onto an aqueous layer coated on the support substrate within the boundary line area, and applying an aqueous medium to the polymer layer to form the two-part structure of the implant precursor. Where the boundary line is formed in vivo on the surface of a tissue defect, an implant precursor formed ex vivo may also be applied to the defect within the area defined by the boundary line. It is preferred that the implant precursor and associated boundary line are manually worked together as the polymer further coagulates to form the solid implant matrix such that the coagulating mass will conform to the contours of the tissue defect and implant site. Preferably, when treating a periodontal bone tissue defect by this method, the boundary line is applied to the root and ligament tissue of the bone defect site.

Implant Precursor-forming Apparatus

According to the invention, a preferred method for making an implant precursor ex vivo is by the use of an apparatus, as shown generally in FIG. 1. It is understood, however, that a variety of shapes, sizes and arrangements of the implant precursor-forming apparatus can be accommodated according to the invention.

FIG. 1 is a schematic drawing of the preferred apparatus design, shown closed as it would be during the coagulation process. The apparatus consists of a case which consists of upper and lower sections (1 and 2) held together by a hinge (3) on one end and a latching mechanism (4 and 5) on the other end. Each section contains a sheet of porous hydrophilic plastic (6 and 7). When the case is closed the two sheets of porous hydrophilic plastic (6 and 7) are held apart by the spacers (8 and 9) as shown in FIG. 1. This apparatus is used by opening the case and filling the pores in the porous hydrophilic plastic sheets (6 and 7) with an aqueous medium. The polymer solution is then dispensed onto the porous hydrophilic plastic sheet in the lower half of the case (7) and the case is closed as shown in FIG. 1. The spacers (8 and 9) define the gap in which the polymer solution is held during the coagulation process and therefore control the thickness of the implant precursor. Once the desired coagulation has elapsed the case is opened and the implant precursor is trimmed and then implanted.

Figure 2:
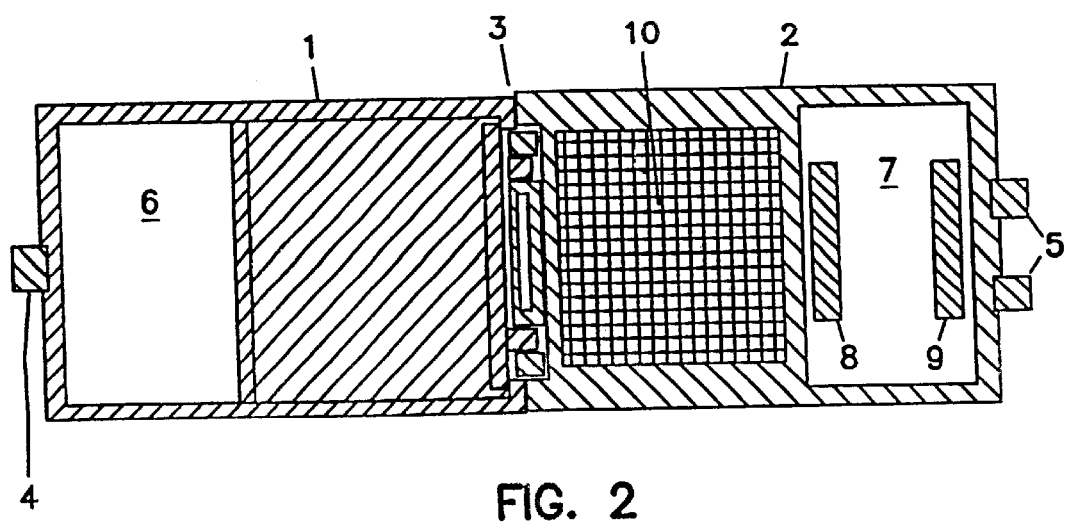
FIG. 2 is a perspective view of the precursor-forming apparatus of FIG. 1, showing the placement of a series of spacers thereon.
Figure 3:
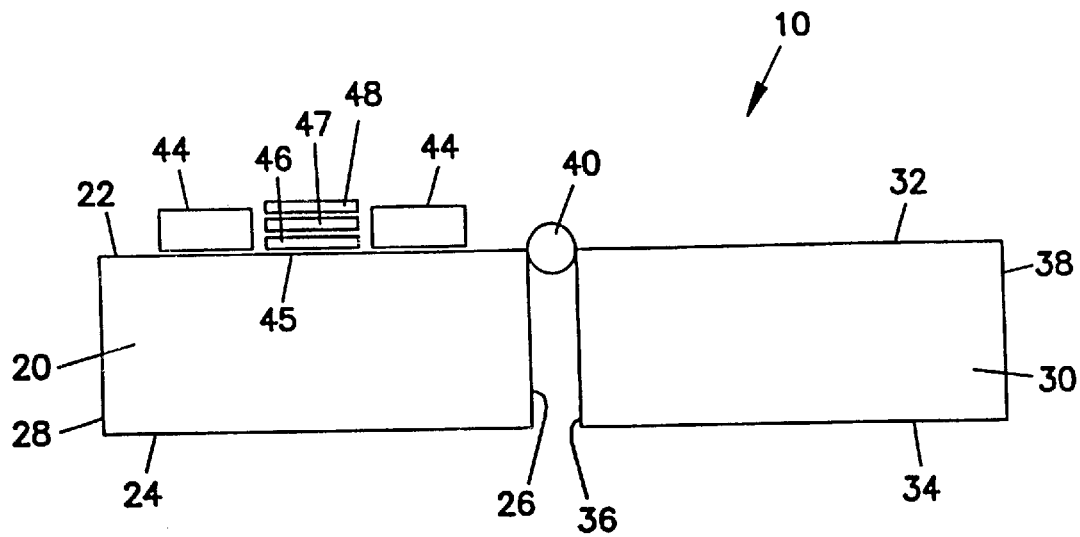
FIG. 3 is a side view of the precursor-forming apparatus of FIG. 2, showing the placement of the aqueous layers and polymer solution layer in the area between the spacers.
Figure 4:
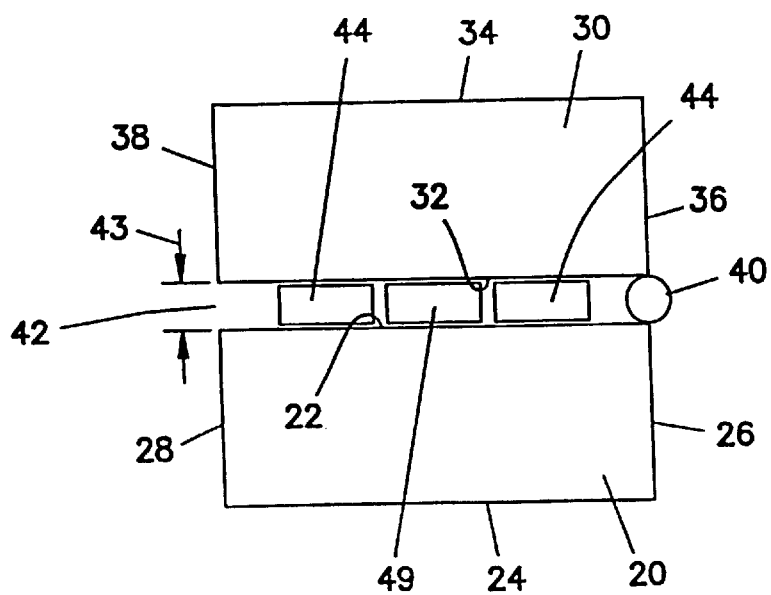
FIG. 4 is a side view of the precursor-forming apparatus of FIG. 3, showing the apparatus in a closed position during formation of an implant precursor.

FIG. 2 details the preferred embodiment of the general apparatus design shown in FIG. 1. The components are labeled with the same numbers as in FIG. 1. This embodiment contains one section (10) which is not present in FIG. 1. It is a trimming grid which is a portion of the case bottom (2). The case consists of an upper and lower section (1 and 2) joined with a hinge (3) formed by snapping the two case sections together. The case is composed of a gamma resistant polypropylene. Alternate case materials which can withstand contact with the polymer solution and sterilization by gamma irradiation and are fairly rigid could be used. The latch mechanism is composed of portions (4 and 5) of the two case sections (1 and 2) which readily snap together and apart to allow opening and closing of the case and hold the case tightly closed during the coagulation process. The hydrophilic porous plastic sheets (6 and 7) are flat, rigid sheets with the hydrophilicity and porosity needed to allow an aqueous medium to fill the pores of the sheet and then allow exchange of the aqueous medium and the solvent between the polymer solution and aqueous medium and the solvent between the polymer solution and aqueous medium in the pores during the coagulation process. The porosity of the sheet is one factor which controls the rate of coagulation. The porous plastic may be of an intrinsically hydrophilic polymer or a blend of a hydrophobic polymer blended with or treated with a surfactant or other agent which increases hydrophilicity. THe material used in the preferred embodiment is a polyethylene blended with a surfactant. The spacers (8 and 9) are rectangles of gamma resistant polypropylene.

The trimming grid (10) is a flat portion of the lower case section (2). After the coagulation process the implant precursor is placed on the trimming grid where it is trimmed to the desire shape, length and width using a surgical prep blade, razor blade or other like means. The trimming grid has a pattern of 1 mm squares which aid in trimming to the desired dimensions. This pattern may be present as part of the case itself or printed onto the case or printed on a label which is then affixed to the case. In the preferred embodiment the pattern is printed on a clear label which is affixed to the underside of the case bottom (2). The pattern is visible through the clear to slightly hazy case bottom (2) and the clear label material. Having the label or printing on the underside of the case eliminates the possibility of physical or chemical interaction of the implant precursor and the label or printing.

The dimensions of the apparatus are dependent on the desired dimensions of the implant precursor. For production of an implant precursor of an approximate thickness of 675 $\mu$m with a length and width of approximately 20 mm or less the following approximate dimensions are appropriate. The spacers (8 and 9) are 675 $\mu$m thick, 0.5 cm wide and 2.5 cm long. The porous plastic sheets are 4.5 cm long and 3.0 cm wide with a thickness of 0.3 cm. The trimming grid pattern (10) is 3.5 cm by 3.5 cm. The case sections (1 and 2) are approximately 7.5 cm by 5 cm with cavities for the porous plastic sheets (6 and 7) 30 cm deep. For proper thickness control the case must be designed to close such that the spacers (8 and 9) are tightly held between two porous plastic sheets (6 and 7) so that the coagulation occurs in a gap which corresponds to the thickness of the spacers.

Adhesive Layer

To enhance adhesion of the implant precursor in the implant site, an adhesive layer may be applied to the surface of the tissue and the formed implant precursor is then placed over the support layer. The adhesive layer preferably helps to maintain the position of the implant precursor as it coagulates to a solid matrix in the implant site. The adhesive layer comprises a bioabsorbable, biodegradable and/or bioerodible substance capable of adhering to both the surface of the tissue defect and to the surface of the implant precursor. An adhesive layer may be formed, for example, by applying a minor but effective amount of the foregoing liquid polymer solution in the form of a bead or as a coating on the surface of the tissue defect.

Support Layer

To maintain the structure and form of the implant precursor or to form the implant precursor directly in vivo, a support layer may be applied to the surface of the tissue and the polymer solution or formed implant precursor is then placed over the support layer. Materials suitable for use in forming a support layer include, for example, a natural body material such as a clot of blood or other body fluid, a water-soluble substance such as gelatin or water-soluble polymer, as for example, polyvinyl pyrrolidone, and other like materials.

A support layer of clotted blood may be formed, for example, by puncturing the tissue with a needle to generate a minor but effective flow of blood which is then allowed to clot. A formed implant precursor, or the liquid polymer solution itself may be applied to the surface of the support layer in the implant site.

In another embodiment, granules or small pieces of a biodegradable porous material such as polylactic acid, oxidized cellulose or gelatin and the like, may be used to fill in a tissue defect or void, and then a formed implant precursor may be applied to the granular support material, or the polymer solution may be dispensed over the support layer to form the implant precursor.

Another useful support layer is a solid matrix having a porous, foam-like structure. Such a matrix may be provided, for example, by mixing air into the foregoing polymer solution to provide a foam-like consistency, and allowing the mixture to coagulate to a matrix having relatively large pores and/or cavities. Air bubbles may be incorporated into the polymer solution, for example, by vigorous stirring the polymer solution, by blowing air into the solution using a syringe, and other like means. It is preferred that an aqueous medium is applied to the surface of the foamed mixture to cause the polymer to coagulate to form a matrix having large cavities.

Large pores may also be provided in a solid support matrix by combining the polymer solution with a gas-forming agent, as for example, a mixture of citric acid and sodium carbonate or bicarbonate. When contacted with an aqueous medium, the gas-forming agent reacts to form gas bubbles such as carbon dioxide within the coagulating polymer matrix.

Where a void space is desirable between the tissue defect and the solid implant, the support layer is preferably formed of a water-soluble, and/or a highly resorbable material. For example, the support layer may comprise a water-soluble substance that will dissolve within a few days, as for example an oxidized cellulose or gelatin material such as Surgicel™ or Gelfoam™, commercially available from Johnson & Johnson Company and the Upjohn Company; a water-soluble polymer such as polyvinyl pyrrolidone, polyethylene glycol, and hydroxypropyl cellulose, and the like; and other like substances. Preferably, the water-soluble support layer will dissolve within about 1–14 days, preferably about 2–4 days, after implantation of the implant precursor.

In cases where it is desired to promote tissue ingrowth into a substrate in the implant site, it is preferred that the support layer comprises a porous material which has a relatively longer rate of degradation. Suitable materials include, for example, a polylactic acid material typically applied to molar extraction sites to inhibit dry sockets, as for example, Drilac™ which is commercially available from THM Biomedical, Inc. and a hydroxyapatite material such as Interpore 200 which is commercially available from Interpore International. Advantageously, a support layer made of a porous material such as polylactic acid or hydroxyapatite, allows the blood to infiltrate and clot within the matrix which provides a source of nutrients to promote tissue ingrowth. It is noted that tissue ingrowth into the support matrix will eventually break down the support layer.

Kit for Forming an Implant Precursor

The invention also includes a kit for forming an implant precursor ex vivo. The kit includes, in combination, (i) a precursor-forming apparatus, as described hereinabove, which is preferably a two-part apparatus hinged along one side; (ii) one or more spacer means for maintaining a gap or space between the two halves of the apparatus, for example, a washer, rod, block, and the like; (iii) one or more vials or other like means containing the aforedescribed polymer solution; and (iv) one or more vials or other like means containing a source of aqueous medium such as water, phosphate buffered saline, and the like. The kit may further include a tweezers or other like means for lifting and holding the formed implant precursor; a device for measuring the dimensions of the tissue defect and/or the implant precursor, as for example, a calibrated tweezers and the like; a gridded template and other like means for measuring the dimensions of the implant precursor; a scalpel, razor blade or other like means for trimming and sizing the implant precursor; and/or a cotton pad or like other means for removing the aqueous medium from the surface of the implant precursor.

Use of the Implant Precursor

The implant precursor may be used for treating a variety of tissue defects. The implant precursor may be applied to an implant site in an animal, such as a void, a defect, surgical incision, and the like, in a hard or soft tissue, by known surgical techniques.

Preferably, once placed in the implant site, the implant precursor will be substantially coagulated to a solid but moldable matrix, within about 0.5–4 hours, more preferably about 0.75–3 hours, even more preferably about 1–2 hours.

For example, the implant precursor may be used in a method for treating a bone tissue defect such as an arm or leg bone fracture, a tooth defect, and the like. Preferably, the bone tissue is surgically separated from the adjacent soft tissue to expose the defect, and the implant precursor is placed into the bone defect, whereupon the implant precursor hardens in situ to a solid implant.

In a preferred use according to the invention, the implant precursor may be used as a barrier system for guided tissue regeneration. The implant precursor may be formed outside the body of the animal and then administered to an implant site such as a tissue with a void such as a periodontal pocket, a soft-tissue defect, a surgical incision, a bone defect and the like. Once administered to the tissue regeneration site, the implant precursor will solidify to form a solid, microporous matrix that provides a surface over which the cell may grow. To enhance regeneration of a hard tissue such as bone tissue, it is preferred that the solid implant matrix provides support for new cell growth that will replace the matrix as it becomes gradually absorbed or eroded by body fluids.

One example of using the implant precursor as a barrier system is in the treatment of a periodontal disease. For such treatment, the gingival tissue overlying the root of the tooth is surgically incised from the tooth root and bone to form a gingival tissue envelope or pocket, and an implant precursor is placed into the pocket and against the bone. After placement, the tissue is sutured to close the pocket, and the implant precursor is allowed to harden to a solid, microporous implant.

The implant precursor may be manipulated in the implant site to conform it to the contours of the tissue defect. For example, in a periodontal defect, the gingival tissue flap may be urged over the solidifying implant matrix placed against the exposed root and bone, and pressure applied to the surface of the overlying tissue onto the solidifying matrix. The solidifying matrix is malleable and such manipulation shapes the implant on one side to conform to the tissue defect and on the other side to the contours of the overlying tissue. The tissue may be retracted to assess the profile (i.e., shape) of the implant matrix and, optionally, additional amounts of the polymer solution may be added to build up the matrix and fill in irregularities as needed. In cases where the implant precursor is too large, a portion of the congealing matrix may be cropped along the edges of the overlying tissue, as for example, just above the gum line of a gingival tissue pocket. The tissue may then be secured in place over the implant matrix, as for example, by suturing the tissue at either end of the pocket to hold the tissue and implant in place.

To aid in the adhesion of the implant precursor to the surface of the tissue defect, a bead or coating of the foregoing polymer solution may be applied over the defect to provide a tacky surface. The implant precursor or liquid polymer solution may then be applied to the surface of bead or coating.

The implant precursor may be used for attaching a skin graft to underlying tissue of a wound; and such use of the implant precursor helps prevent seroma or hematoma formation, and speed the healing process. Preferably, the implant precursor includes a topical antibiotic agent.

The implant precursor may also be used to enhance closure of a surgical incision as, for example, an incision through the sternum for open heart surgery, by stabilizing the sternum and promoting healing. In such use, the implant precursor is applied to the two sides of the sternum prior to closure of the sternum with metal wires and/or sutures. Preferably, the implant precursor includes a growth factor and/or an antibiotic agent.

Advantageously, the implant precursor provides a means of adhering an implant article to a tissue generally covered with a mucous layer, as for example, a gingival tissue. Also, the implant precursor provides for the application of a liquid polymer solution in an implant site without the uncontrolled flow of liquid into areas other than those identified for treatment. For example, in the treatment of a periodontal defect, use of the present implant precursor will advantageously avoid the accumulation of a polymer solution into spaces between tooth roots and the periodontal region where the ligament cells are located. The present precursor implant also facilitates a better match of a barrier implant in a tissue defect site than other devices known and used in the art.

The microporous polymer matrix of the implant is capable of biodegradation, bioerosion and/or bioabsorption within the implant site of the animal. The particular polymer and the molecular weight of the polymer may be varied according to the desired duration or time interval for maintaining the solid polymer matrix within the implant site, as for example, a few days or weeks to several years. When the implant is used to enhance cell growth and tissue regeneration, it is preferred that the polymer matrix will disintegrate at a rate effective to allow displacement of the matrix by cell growth from the adjacent cells or tissue.

Formulation of the liquid polymer solution for preparing the implant precursor, and administration of the implant precursor and polymer solution in vivo will ultimately be according to the judgment and protocol of the patient's attending health care professional such as a physician, or if appropriate, a dentist. Choice of the particular formulation of ingredients will be made by the attending health care professional. Without a bioactive agent, the solid implant resulting from the implant precursor can function as a structure for promotion of cell growth and tissue repair. With a bioactive agent, the implant will not only function in such capacity but will also convey the properties of the bioactive. Thus, the present invention relates to a polymer system for the controlled delivery of bioactive materials.

The amounts and concentrations of ingredients in implant precursor administered to the patient will generally be effective to accomplish the task intended. If that task is to fill a void space, an implant precursor of an appropriate size and an effective amount of ingredients will be administered to accomplish this task. For administration of a bioactive agent, the amounts and release rates will follow recommendations of the manufacturer of the bioactive agent. Generally, the concentration of a bioactive agent in the liquid polymer solution will be about 0.01–400 mg per gram of polymer solution.

The invention will be described with reference to various specific and preferred embodiments and techniques. However, it should be understood that many variations and modifications may be made while remaining within the spirit and scope of the invention.

EXAMPLE 1

Ex vivo Formation of an Implant Precursor With a Porous Polyethylene Substrate

A polymer mixture comprising about 37% poly(DL-lactide) (DL-PLA) and about 63% N-methyl-2-pyrrolidone (NMP) was prepared. The DL-PLA had a molecular weight of about 65,000 daltons (inherent viscosity in chloroform of about 0.50 dL/g). Polypropylene containers were filled with this polymer mixture such that each contained about 0.8 g of the polymer mixture. These filled containers were then sterilized by exposure to gamma radiation at a level of 25–35 kGy, which result in a final molecular weight of the DL-PLA of about 38,000 daltons (inherent viscosity in chloroform of about 0.34 dL/g).

The apparatus diagrammed in FIG. 2 was used to form an implant precursor from the liquid polymer mixture. The porous polyethylene-substrates on each side of the case were saturated with about 2.5 mL of sterile saline. Two polypropylene spacers were placed on the porous polyethylene substrate on the lower half of the case (nearest to the trimming grid) such that they were parallel to the hinge of the case and against the edges of the porous polyethylene substrate. A filled container of the polymer mixture was opened, and the contents (approximately 0.6 g) were expelled onto the center of the porous polyethylene substrate between the spacers. The case was closed and latched, and was then reopened after six minutes. The semi-rigid article was removed from the porous polyethylene substrate, placed onto the attached trimming area, and trimmed to size using a sterile razor blade.

The implant precursor was examined visually; it was opaque, semi-rigid, and flexible. The implant precursor had a two-part structure which consisted of a gelatinous, semi-rigid outer layer and a more liquid center core. Chemical analysis indicated that the implant precursor contained about 58% NMP.

EXAMPLE 2
In Vitro Formation of an Implant Precursor

An implant precursor was formed as in Example 1 above, except that the case remained closed for eight minutes. This article was more rigid than the article from Example 1 above.

EXAMPLE 3
In Vitro Formation of an Implant Precursor

An implant precursor was formed as in Example 1 above, except that the case remained closed for four minutes. This article was less rigid than the article from Example 1 above.

EXAMPLE 4
In Vitro Formation of an Implant Precursor With a Glass Substrate

Two spacers with approximate thicknesses of 430 $\mu$m were constructed by gluing two sets of three glass microscope cover slips together. These were placed on a glass microscope slide leaving a space between them. Approximately 0.3 g of the same polymer mixture as in Example 1 was then dispensed onto the microscope slide between the spacers using a syringe. An atomizer was used to spray the polymer mixture with water three times. After 30 seconds the water spraying was repeated. After an additional 30 seconds, another microscope slide was sprayed with water and then pressed onto the coagulating polymer mass and the spacers. This second microscope slide was held in place for 60 seconds and then removed. The coagulating polymer mass was then sprayed with water three times and allowed to set for 60 seconds. The three water sprays and 60 second set was then repeated. The glass microscope slide and the coagulating polymer mass were then placed over a grid of 1 mm squares. A sterile razor blade was then used to trim the polymer mass to the desired size and shape. The cut piece was then sprayed with water three times and allowed to set for 60 seconds. The excess water was then removed using a gauze pad. The opaque and flexible implant precursor was then ready for implantation.

EXAMPLE 5
In Vitro Formation of an Implant Precursor With a Glass Substrate

A 2 inch×3 inch microscope slide with a 20 mm×20 mm graph inscribed on the underside is placed on a 2 inch×3 inch×¼inch Gray-Lite #14 dark background glass. On the top side of the microscope slide were placed 1 inch diameter 750 micron stainless steel washers. A washer is placed on the left and right of the inscribed graph. A polymer mixture prepared as described in Example 1 was then layered over the microscope slide and smoothed to remove any bubbles or uneven areas. Sterile isotonic saline was carefully dropped onto the middle of the liquid polymer layer where it flowed laterally to cover the entire film. The saline was allowed to stay in contact with the polymer mixture for 1 minute at which time the outside surface or skin became opaque. The excess saline was then carefully removed by air spray or sponge and the entire process repeated again with addition of more polymer mixture and saline to coagulate the polymer. After the second layer had set for 1 minute, a 1 inch×3 inch regular microscope glass slide moistened with saline solution was placed over the polymer mixture and compressed to the height of the stainless steel washers (750 $\mu$m). Additional saline was added to the edge of the regular microscope glass slide to saturate the underside of the slide. The compressed material was allowed to set for 10 more minutes. The regular microscope slide and washers were then removed and the implant precursor film was cut with a single razor blade to the dimensions of the periodontal defect.

EXAMPLE 6
Application of an Implant Precursor to a Periodontal Defect

A mandibular first molar of a 65-year old man was selected for treatment because of long-standing pocket depth and furcation involvement. During surgery, a full-thickness periodontal flap was elevated, the defect scaled and root planed, and the dimensions of the defect measured. A customized implant precursor barrier membrane prepared according to Example 5 was applied over the periodontal defect so as to approximate the level of the crown margin and overlay the osseous margins by 2 to 3 mm. The precursor material adhered directly to the tooth and bone without the need for suturing in place. The buccal flap was replaced over the defect and the implant precursor and sutured to the lingual tissue. A periodontal dressing material was applied to the surgical area and systemic antibiotic therapy was used for 7 days. After one week, the fully formed barrier was in place. At one month, the barrier was also present but displaced buccally from the tooth surface because of the formation of granulation tissue between the barrier and the root surface. At the 6-month examination, the barrier was no longer evident and epithelium had grown over the former area of granulation tissue. The clinical probing measurements at this time showed that the periodontal pocket depth had decreased from 5 mm to 2 mm and the level of attachment of tissue to the tooth had increased from 7 mm to 4 mm. The horizontal furcation depth had also decreased from 5 mm to 3 mm. All clinical measurements indicated good tissue regeneration at the defect site.

EXAMPLE 7
Treatment Using an Implant Precursor in Combination With a Support Layer A polymer mixture may be prepared as described in Example 1. A thigh bone of an anesthetized male rat may be surgically incised to create a defect. Granules of Surgicel™ oxidized cellulose may be applied to the defect to stop the bleeding and to fill in the defect. A precursor implant prepared as described in Example 1 may be applied over the surface of the Surgicel™ support layer. The tissue is then replaced and sutured in place. The implant precursor will further solidify to a solid barrier matrix.

EXAMPLE 8
Treatment in Which the Implant Precursor is Formed In Vivo over a Support Layer A thigh bone of an anesthetized male rat may be surgically incised to create a defect and granules of Surgicel™ oxidized cellulose may be applied to the defect to stop the bleeding and to fill in the defect. A polymer mixture prepared according to Example 1 may then be applied directly over the surface of the Surgicel™ support layer. The moisture from the tissue defect will cause the liquid polymer to partially solidify to form the same type of implant precursor as described in Example 1. The soft tissue is then replaced and sutured into place. The implant precursor thus formed will further solidify to a solid barrier matrix.

EXAMPLE 9
Treatment With an Implant Precursor Comprising a Biological Agent

A polymer mixture may be prepared as described in Example 1. To this mixture may be added 5% by weight doxycycline hyclate. An implant article may then be prepared in vivo from the drug/polymer mixture as described in Example 1. The implant article may be placed into a periodontal defect as described in Example 6. The doxycycline will be dispensed from the solid barrier implant as it degrades and provide protection against bacterial infection.

EXAMPLE 10
In Vivo Formation of an Implant Precursor in a Bone

A polymer mixture may be prepared as described above in Example 1.

A thigh bone of an anesthetized male rat may be surgically incised, and the surface of the incision of the bone tissue may be coated with a thin layer of a phosphate buffered saline (PBS) solution. The polymer mixture (about 1–3 ml) may be dispensed from a syringe or eye dropper onto the surface of the water-coated bone tissue. The buffer solution (about 1–3 ml) may be dispensed onto the layer of the polymer mixture. After 2–5 minutes, the polymer mixture will coagulate to form a gelatinous outer layer with a liquid content of an implant precursor.

The implant precursor may be covered with tissue, and the tissue sutured in place. The implant precursor will gradually solidify to a solid matrix. After 5–10 days, the implant site may be reopened, and the implant article mass should have been displaced by the ingrowth of bone tissue.

What is claimed is:

1. An implant precursor comprising a mixture of a biocompatible, biodegradable, water coagulable thermoplastic polymer, a pharmaceutically-acceptable organic solvent capable of diffusing into tissue fluid, and a release rate modification agent wherein the implant precursor has a structure of an outer sac and a liquid content.

2. The implant precursor according to claim 1 further comprising a biologically-active agent.

3. The implant according to claim 2 wherein the biologically-active agent is selected from the group consisting of an antibacterial agent, an antifungal agent, an antiviral agent, an anti-inflammatory agent, an antiparasitic agent, an anti-neoplastic agent, an analgesic agent, an esthetic agent, a vaccine, a central nervous system agent, a growth factor, a hormone, an antihistamine, an osteoinductive agent, a cardiovascular agent, an anti-ulcer agent, a bronchodilating agent, a vasodilating agent, a birth control agent, and a fertility-enhancing agent.

4. An implant precursor according to claim 1 wherein the implant precursor is surrounded by tissue.

5. An in situ formed implant comprising a mixture of a biocompatible biodegradable, water-coagulable thermoplastic polymer, a biologically active agent and a release rate modification agent, wherein the implant has a two part structure composed of an outer sac and a liquid content.

6. An in situ formed implant according to claim 5 wherein the liquid content is a mixture of at least the thermoplastic polymer, the biologically active agent and the release rate modification agent.

7. An implant precursor according to claim 4 wherein no organic solvent is present.

8. An implant precursor according to claim 4 wherein the organic solvent has dissipated into the tissue.

9. An implant precursor according to claim 1 wherein the organic solvent and the release rate modification agent are the same.

10. An implant precursor according to claim 9 wherein the implant precursor is surrounded by tissue.

11. An implant precursor according to claim 1 which is formed by direct administration, into a body tissue, of a liquid polymer solution comprising the polymer, organic solvent, and release rate modification agent.

12. An implant precursor according to claim 11 wherein the organic solvent and release rate modification agent are the same.

13. An implant precursor according to claim 4, 7, 8, 9, 10, 11 or 12 wherein the mixture further comprises a bioactive agent.

14. An in situ formed implant comprising a mixture of a biocompatible biodegradable, water-coagulable thermoplastic polymer, a biologically active agent and an organic solvent that is capable of diffusion into body fluid, wherein the implant has a two part structure composed of an outer sac and a liquid content.

15. An implant according to claim 14 wherein the mixture further comprises a release rate modification agent.

16. An implant according to claim 15 wherein the organic solvent and release rate modification agent are the same.

17. An implant according to claim 5 wherein the liquid content has a watery or viscous character.

18. An implant according to claim 17 wherein the liquid content has a viscous character.

19. An implant according to claim 5 wherein the implant has become a solid.

20. An implant according to claim 5 wherein the release rate modification agent is a water-soluble, water-miscible or water insoluble organic substance.

21. An implant according to claim 20 wherein the release rate modification agent is a water insoluble organic substance.

22. An implant according to claim 21 wherein the water insoluble organic substance is an ester of a mono-, di- or tricarboxylic acid.

23. An implant according to claim 16 wherein the organic solvent/release rate modification agent is an ester of a mono-, di- or tricarboxylic acid.

24. An implant precursor according to claim 9 wherein the organic solvent has a Hildebrand solubility ratio from about 9 to about 13.

25. An implant precursor according to claim 9 wherein the organic solvent/release rate modification agent is an ester of a mono-, di- or tricarboxylic acid.

26. An implant according to claim 16 wherein the liquid content has a watery or viscous character.

27. An implant according to claim 26 wherein the liquid content has a viscous character.

28. An implant according to claim 16 wherein the implant has become a solid.

* * * * *

UNITED STATES PATENT AND TRADEMARK OFFICE
CERTIFICATE OF CORRECTION

PATENT NO. : 6,395,293 B2
DATED : May 28, 2002
INVENTOR(S) : Alan M. Polson et al.

It is certified that error appears in the above-identified patent and that said Letters Patent is hereby corrected as shown below:

Title page,
Item [56], References Cited, U.S. PATENT DOCUMENTS, delete ", et al." after "Baker".
OTHER PUBLICATIONS, delete "33(4)1" and insert -- 33(4) --, therefor.
Item [63], Related U.S. Application Data, lines 6-9, delete the following:
", and a continuation-in-part of application No. 07/783,512, filed on Oct. 28, 1991, now Pat. No. 5,324,519, which is a continuation-in-part of application No. 07/384,416, filed on Jul. 24, 1989, now Pat. No. 5,077,049".

Column 1,
Line 6, delete "08//883,260" and insert -- 08/883,260 --, therefor.
Lines 12-15, and delete the following:
", a continuation-in-part of U.S. patent application Ser. No., 07/783,512, filed Oct. 28, 1991, which is a continuation-in-part of U.S. patent application Ser. No. 07/384,416, filed Jul. 24, 1989 (now U.S. Pat. No. 5,077,049)".

Column 2,
Line 36, delete "may-be" and insert -- may be --, therefor.

Column 4,
Line 65, insert -- . -- after "like".

Column 7,
Line 22, delete "comprising-an" and insert -- comprising an --, therefor.

Column 15,
Line 39, insert the following paragraph after "bone defect site.":
-- In another embodiment of the invention, the liquid polymer solution can be administered as a liquid directly into body tissues or cavities wherein an implant precursor and/or implant is formed *in situ* by interaction of the liquid polymer solution with tissue fluid. Alternatively, the liquid polymer solution can be externally combined with an aqueous medium as described above to form an implantable polymer precursor. The implantable precursor is then inserted surgically into the body as described above. --

UNITED STATES PATENT AND TRADEMARK OFFICE
CERTIFICATE OF CORRECTION

PATENT NO. : 6,395,293 B2
DATED : May 28, 2002
INVENTOR(S) : Alan M. Polson et al.

It is certified that error appears in the above-identified patent and that said Letters Patent is hereby corrected as shown below:

<u>Column 16,</u>
Line 25, delete "THe" and insert -- The --, therefor.

Signed and Sealed this

Eleventh Day of February, 2003

JAMES E. ROGAN
*Director of the United States Patent and Trademark Office*